United States Patent [19]
Ries

[11] Patent Number: 5,234,898
[45] Date of Patent: Aug. 10, 1993

[54] METHOD FOR THE TREATMENT OF PLANT PARTS WITH L(+) ADENOSINE TO IMPROVE QUALITY

[75] Inventor: Stanley K. Ries, East Lansing, Mich.

[73] Assignee: Board of Trustees operating Michigan State University, East Lansing, Mich.

[21] Appl. No.: 819,997

[22] Filed: Jan. 13, 1992

[51] Int. Cl.$^5$ .................. A01N 43/08; A23B 7/154
[52] U.S. Cl. ............................... 504/297; 426/321
[58] Field of Search ........................ 71/88; 504/297; 426/321

[56] References Cited

U.S. PATENT DOCUMENTS

| | | | |
|---|---|---|---|
| 4,150,970 | 4/1979 | Ries et al. | 71/122 |
| 4,333,758 | 6/1982 | Welebir | 71/80 |
| 4,741,754 | 5/1988 | Ries | 71/79 |
| 4,849,012 | 7/1989 | Wilson | 71/122 |
| 5,009,698 | 4/1991 | Ries et al. | 71/92 |

OTHER PUBLICATIONS

Ries et al. "9-β-L(+)Adenosine: A new naturally occurring plant growth substance elicited by triacontanol in rice" *Plant Growth Regulation* 9:263-273, 1990.
Ries, S. K., Plant Physiol. 95, 986 (1991).
Ries, S. K. and V. F. Wert, Plant Growth Reg. 10, In Press (1991).
Evans, D. E., et al., J. Exp. Bot. 42, 285 (1991).
Braam, J., et al., Cell 60, 357 (1990).
Mitchell, C. A., et al., J. Amer. Hort. Sci. 100, 161 (1975).
Schroeder, J. I., et al., The Plant Cell 3, 555 (1991).

*Primary Examiner*—Richard L. Raymond
*Assistant Examiner*—S. Mark Clardy
*Attorney, Agent, or Firm*—Ian C. McLeod

[57] ABSTRACT

A method for the treatment of a plant with L(+) adenosine to improve the quality of the parts at the extremities of the plant, such as fruit, vegetables (including root vegetables) and leaves. The method includes applying L(+) adenosine to the plant or part of the plant prior to harvest of the fruit or vegetable. Increases in mineral pulses in the terminal parts of the plant produce the increase in quality.

9 Claims, 6 Drawing Sheets

METHOD FOR THE TREATMENT OF PLANT PARTS WITH L(+) ADENOSINE TO IMPROVE QUALITY

BACKGROUND OF THE INVENTION (1) Field of the Invention

The present invention relates to a method for the treatment of parts of a plant shortly prior to harvest to improve the quality of the parts, particularly the firmness and storage stability of the part, by increasing the cation concentrations at the extremities of the plant. In particular, the present invention relates to the use of L(+)adenosine to increase the firmness and storage stability of fruits and vegetables.

(2) Prior Art

U.S. Pat. No. 4,849,012 to Wilson describes the use of triacontanol applied to the trees and fruits to increase the sugar content in oranges. The use of triacontanol and trim to stimulate plant growth is described in U.S. Pat. Nos. 4,150,970 to Ries et al and 4,741,754 to Ries. U.S. Pat. No. 4,333,758 to Welebir also shows triacontanol compositions.

U.S. Pat. No. 5,009,698 to Ries, Wert and Nair, describes the use of L(+)adenosine to stimulate the growth of a plant. The L(+)adenosine is applied early in the growth of the plant and produces significant yield improvements.

Triacontanol (TRIA) is used on millions of hectares to increase crop yield, particularly in Asia. In controlled environment studies, synthetic L(+) adenosine was found to increase the rate of growth of rice seedlings as measured by total dry weight gain, more than 50% within 24 hours of a foliar application of 0.01 to 100.0 $\mu g \cdot L^{-1}$ ($3.7 \times 10^{-11}$ to $10^{-7}$M) (Ries, S. K., et al., Plant Growth Reg. 263 (1990)). L(+) adenosine has shown promise in early field trials to be more consistent than TRIA.

OBJECTS

It is therefore an object of the present invention to provide a method which increases the firmness, storage stability and shelf life of fruits and vegetables.

It is further an object to provide a method which is simple and economic for use in the field (farm, ranch or grove) or in the greenhouse.

These and other objects will become increasingly apparent by reference to the following description and the drawings.

GENERAL DESCRIPTION

The present invention relates to a method for improving the quality of a part which is to be removed from a plant which comprises: (a) applying L(+)adenosine to the plant before the part is removed in an amount sufficient to increase ion concentrations at extremities of the plant; and (b) harvesting the part soon after the application to thereby improve the quality of the part.

Further, the present invention relates to a method for inhibiting spoilage which is associated with a lack of firmness of a skin of the plant in a harvested part severed from a plant which comprises: applying L(+)adenosine to the plant in an amount sufficient to increase puncture resistance of a skin of the part and to inhibit the spoilage of the part of the plant to be harvested; and harvesting the plant part soon after the application.

Since the discovery of the plant growth regulating properties of triacontanol (TRIA) and later its second messenger 9-$\beta$-L(+) adenosine [(9H-purin-6-amine, 9-$\beta$-L ribofuranosyl, L(+) adenosine)], there has been the enigma of the extremely rapid responses (Ries, S. K., Plant Physiol. 95, 986 (1991)). It is now believed that nanomolar concentrations of L(+) adenosine (MW, 267) act by indirectly causing changes in the concentration of several ions within the apoplastic solution phase (xylem solution) of plant tissue.

The treatment is between 0.1 and 60 days before harvest, preferably 1 to 30 days. Longer times do not appear to produce significant results.

The L(+)adenosine can be synthetically prepared as described in U.S. Pat. No. 5,009,698. Usually it is in high purity and free of inhibitory compounds. The amount of L(+)adenosine is provided between about 0.01 to 10,000 micrograms per liter in an aqueous solution. The L(+)adenosine is applied in a spray in most instances although other methods can be used.

The present invention results from the fact that the mineral ion fluxes in the plant increase upon application of L(+)adenosine to the plant thereby increasing the levels of these ions in the fruit an vegetables at the extremities of the plant. The increased level of mineral ions in the fruits or vegetables provides a longer shelf life and firmness.

SPECIFIC DESCRIPTION

The following Examples 1 to 7 show the increases in mineral ion pulses as a function of time in various plants.

EXAMPLE 1

Applications of picomole quantities 9-$\beta$-L(+) adenosine, the second messenger elicited by triacontanol, to tomato foliage increase $Ca^{2+}$, $Mg^{2+}$ and $K^+$ in the exudate from cut stems of tomato and cucumber seedlings by 20 to 60%. The increase in $Ca^{2+}$ and $Mg^{2+}$ from the L(+) adenosine treatment occurred when the plants were cut within 5 s after application in the first 10-20 $\mu$l of exudate collected within 1 to 2 minutes after the plants were excised. The increase in the concentration of $K^+$ in the exudates, due to the L(+) adenosine treatment, did not occur until the 40 to 60 $\mu$l fraction of the exudate was collected. When plants were cut at different times after application of L(+) adenosine, the difference in $Ca^{2+}$ and $Mg^{2+}$ concentrations due to L(+) ado treatment decreased within 12 minutes of application, whereas the difference in K. concentration increased. The difference in concentration of all ions was minimal in exudates taken 25 minutes after the stem was excised and absent after 24 hours.

There was a clear response of tomatoes to the dose of L(+) adenosine with an optimum concentration of 100 $\mu$g L: ($3.7 \times 10^{-7}$M). The enantiomer of L(+) adenosine, 9-$\beta$-D(-) adenosine had no effect on the ion fluxes in tomato and inhibited the effect of 9-$\beta$-L(+) adenosine on ion fluxes at equimolar concentrations.

'Sunny' tomatoes (*Lycopersicon esculentum* Mill.) and 'Flurry' cucumbers (*Cucumis sativus* L.) were grown in a greenhouse under approximately 16 hours of 700 $\mu$mol·sec$^{-1}$m$^{-2}$ of supplemental light (metal halide). Several seeds were planted in 15.0 cm diameter clay pots and thinned to 2 or 3 plants 8 to 10 days after emergence. Soluble fertilizer (200 ml of 1.0 g L$^{-1}$ of 20—20—20 was applied once or twice after planting and again the day prior to treatment. Twenty to 25 days after planting the plants (3-4 true leaves) were watered with nutrient solution again. The pots were labeled, randomized for treatments within blocks and isolated on the greenhouse bench so they were not touching. They were not disturbed prior to the initiation of the experiments.

Plants were treated at previously selected random locations on the greenhouse bench, with a minimum of 3 replicates of 2 to 3 plants per treatment. Prior to treatment, the plants were surrounded on 3 sides and the top with cardboard to prevent the mist from the sprayer (an adjustable linear polyethylene aerosol "Trigger" sprayer from Scientific Products Co., Chicago) from contacting neighboring plants. The plants were not sprayed to drip. For example, 26-day-old tomato plants retained about 350 $\mu$l of spray. All experiments discussed here were conducted 8 to 12 hours into the photoperiod because it had been previously shown that plants respond best to L(+) adenosine at this time (Ries, S. K. and V. F. Wert, Plant Growth Reg 10, In press (1991)). The plants were sprayed with synthetic L(+) adenosine, (>99% pure by HPLC analysis) (The Vigoro Corporation, Winter Haven, Fla. 33882), synthetic D(-) adenosine (>99% pure by HPLC analysis) (Aldrich Corp., Milwaukee, Wisc. 53233).

To collect exudate, the plants were excised with a razor blade 2.0-3.0 cm below the cotyledonary node at the surface of the dry vermiculite. The exudate from the cut stem were collected with adjustable micro pipettes, usually in successive 10 or 20 $\mu$l aliquots, which were available within 1 to 2 minutes after excision. The exudate from all of the shoots (2 or 3) in each pot was placed in 5.0 ml of deionized water. An aliquot of this was added to a solution of LaCl$_3$ (1000 mg L$^{-1}$) for $Ca^{2+}$ and $Mg^{2+}$ analysis or CsCl (1000 mg (L$^{-1}$) for $K^+$ analysis by atomic absorption/emission spectrophotometry (Video 12, Instrumentation Lab Inc., Wilmington, Mass. 01887).

Dose response studies showed that the optimum concentration of L(+) adenosine was about 100 $\mu$g L$^{-1}$ as shown in Table 1.

TABLE 1

| L(+) adenosine concentration ($\mu$g L$^{-1}$) | Ion concentration (mM) | | |
|---|---|---|---|
| | $Ca^{2+}$ | $Mg^{2+}$ | $K^+$ |
| 0.0 | 1.34 | 1.88 | 18.8 |
| 1.00 | 1.63 | 1.92 | 19.3 |
| 10.0 | 1.77 | 2.11 | 19.0 |
| 100 | 2.21 | 2.67 | 20.9 |
| 1000 | 1.65 | 1.24 | 19.7 |
| LSD .05 | .42 | .36 | NS |
| LSD .01 | .62 | .52 | |

The F value for the quadratic trends of $Ca^{2+}$ and $Mg^{2+}$ with L(+) adenosine concentration is significant at $P \leq 01$. The $Ca^{2+}$ and $Mg^{2+}$ concentration in the exudates was less at 1000 $\mu$g L$^{-1}$ of L(+) adenosine. At the optimum concentration each picomole of L(+) adenosine applied to the foliage causes a difference of more than 100 picomoles of $Ca^{2+}$ and $Mg^{2+}$ in the first 20 $\mu$l of exudate. There was no significant difference in $K^+$ concentration as shown in Table 1.

EXAMPLE 2

Early studies revealed that it was not possible to cut the plants quickly enough to obtain similar ion concentrations in exudates from control plants sprayed with water and those treated with L(+) adenosine. The only "zero time" control that proved to be the same as the water control was to cut the plants and hold them over the cut stems prior to spraying with L(+) adenosine.

Figure 1A:
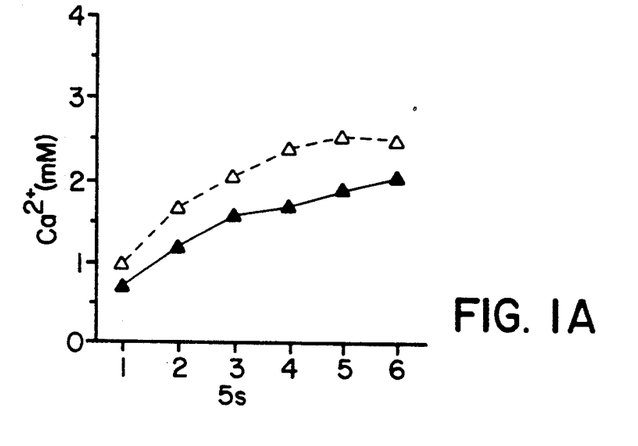
FIGS. 1A to 1I show the ion concentration in successive 20 $\mu l$ fractions from 24-day-old tomato plants excised at 5 seconds, 12 minutes and 24 minutes after treatment with $H_2O$ or 100 $\mu g\ L^{-1}$ L(+) adenosine. Each observation is average of 2 plants in each of 3 replicates. The F values for the main effect of L(+) adenosine vs. control were significant at $P \leq 0.01$ for all $Ca^{2+}$ times, and for 5 seconds $Mg^{2+}$. The F value for the difference in $K^+$, concentration between control and L(+) adenosine treatments with different exudate fractions was significant at $P \leq 0.01$ for both the 5 second and 12 minute treatments.
Figure 1B:
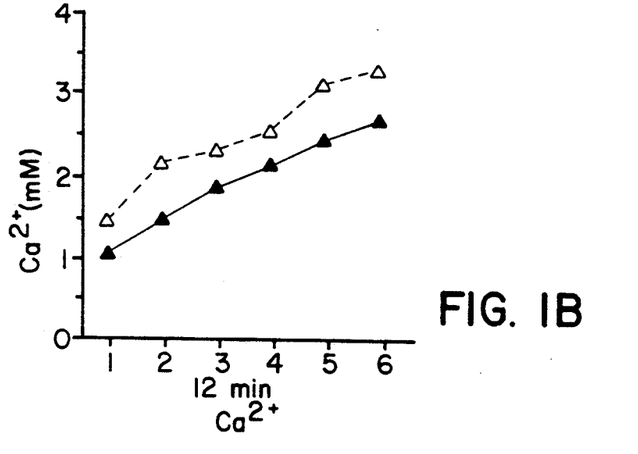
Figure 1C:
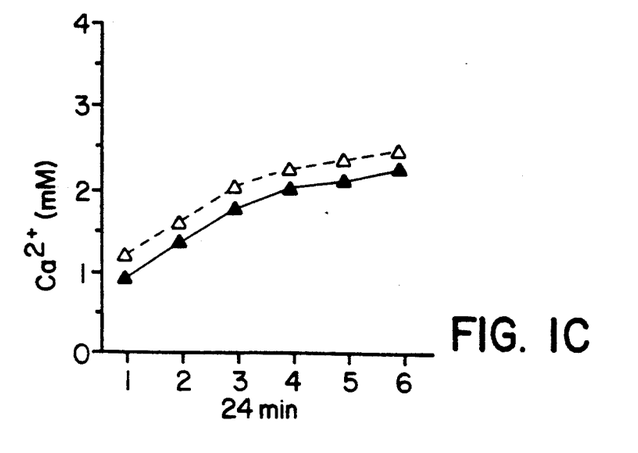
Figure 1D:
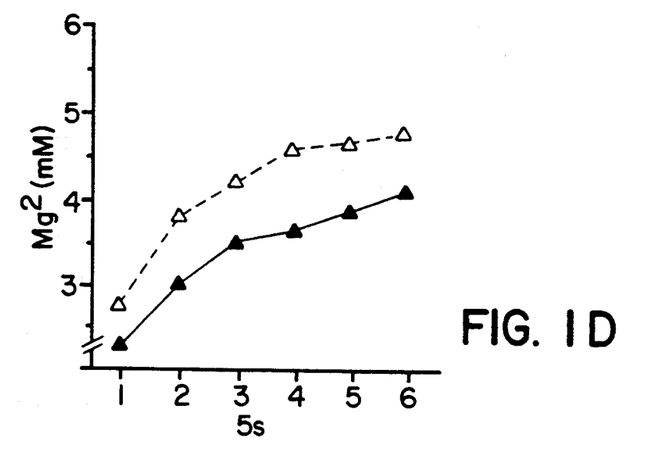
Figure 1E:
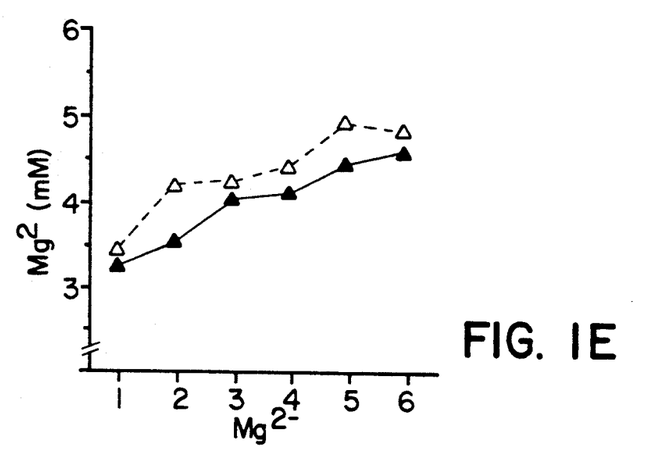
Figure 1F:
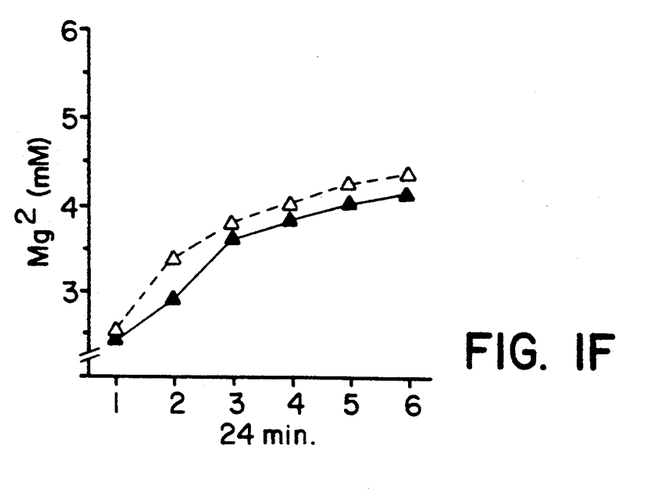
Figure 1G:
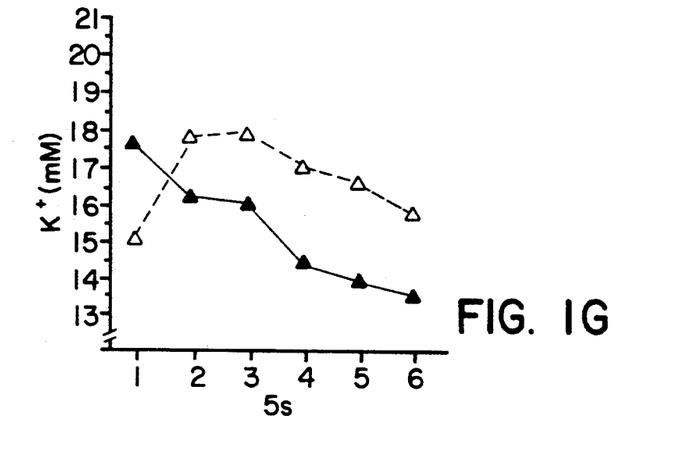
Figure 1H:
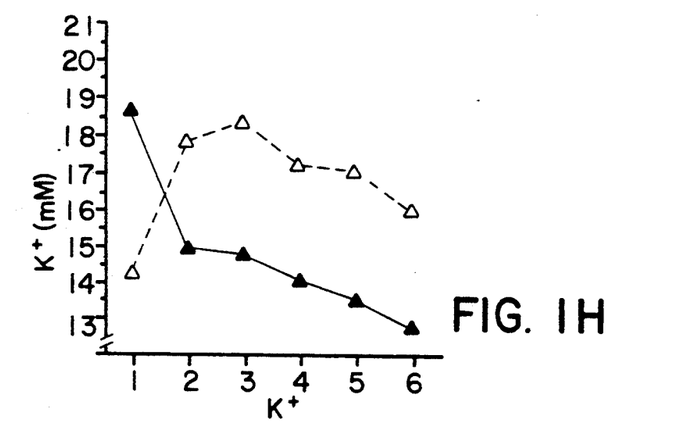
Figure 1I:
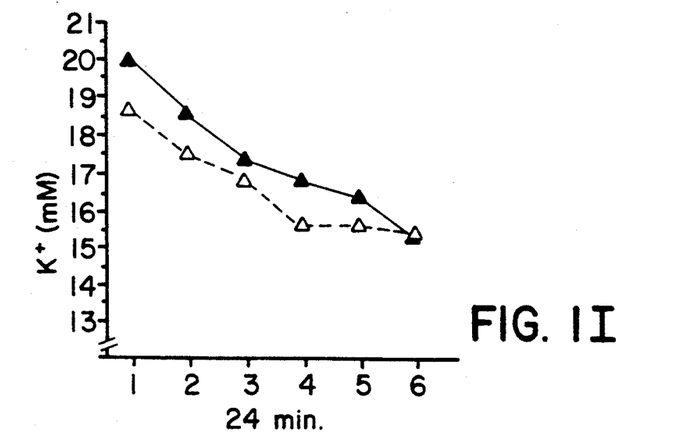

Several experiments showed that ion concentration varied depending on the time the plant was excised after treatment. When the exudate was collected from plants cut 5 seconds after spraying with either water or L(+) adenosine the first 20 $\mu$l contained about 40% more $Ca^{2+}$ and 20% more $Mg^{2+}$ than controls sprayed with water as shown in FIGS. 1A to 1H. These same exudates showed significantly less $K^+$ in the first 20 $\mu$l of exudate from L(+) adenosine treated plants. However, by the fourth 20 $\mu$l fraction the $K^+$ concentration in the L(+) adenosine treatment was more than 2 mM higher than the control (FIGS. 1A to 1I). $Ca^{2+}$ and $Mg^{2+}$ concentration at all times increases with successive fractions whereas the $K^+$ concentration decreases in the controls with successive fractions. Twenty-four minutes after treatment with L(+) adenosine, there is little difference between the ion concentration in controls and treatments, indicating that L(+) adenosine caused a pulse of ions which could not be detected after 24 minutes (FIGS. 1C, 1F and 1I). In the first 100 $\mu$l of exudate one picomole of L(+) adenosine increased the quantity of $Ca^{2+}$ and $Mg^{2+}$ by more than 2,000 picomoles and $K^+$ more than 40,000 picomoles. In a study where plants were excised 5 seconds, 24 hours and 48 hours after treatment with water or L(+) adenosine, only the 5 second L(+) adenosine treatment showed significantly higher ion concentrations (data not shown).

EXAMPLE 3

Various controls were used to establish whether or not there was an artifact in the protocol. Perhaps the best control was synthetic $D(-)$ adenosine the enantiomer of $L(+)$ adenosine. Equimolar concentrations of $D(-)$ adenosine had no effect on the ion concentration in the exudate from the cut stems. In a test where the plants were severed 5 seconds after spraying with 10 $\mu g \cdot L^{-1} L(+)$ adenosine or a mixture of $L(+)$ adenosine and $D(-)$ adenosine the average concentration of $Ca^{2+}$ in the water control, $L(+)$ adenosine and the equimolar mixture was 2.54, 3.89 and 2.69 mM, respectively. The F value for the difference of the $L(+)$ adenosine treatment from the other treatments was significant as $P \leq 0.01$. In another test, a higher concentration of $L(+)$ adenosine was used (100 $\mu g\ L^{-1}$) to determine if the inhibition by $D(-)$ adenosine (10 $\mu g\ L^{-1}$) could be overcome. The $Ca^{2+}$ concentrations in the $H_2O$, $L(+)$ adenosine, $D(-)$ adenosine and mixture of $L(+)$ and $D(-)$ adenosine were 1.72, 2.32, 1.62 and 1.84 mM, respectively. The F value for the comparison of the $L(+)$ treatment with others was significant at $P \leq 0.01$. Further tests with both cucumbers and tomatoes showed that 1.0 $\mu g\ L^{-1}$ of $D(-)$ adenosine inhibited the activity of $L(+)$ adenosine at 10, 100 and 1000 $\mu g\ L^{-1}$, as measured by $Ca^{2+}$ and $Mg^{2+}$ concentration in the exudate (data not shown). Thus, the primary form of adenosine ($D(-)$ adenosine) found in plants inhibits the activity of $L(+)$ adenosine when the two are applied together exogenously.

EXAMPLE 4

Figure 2:
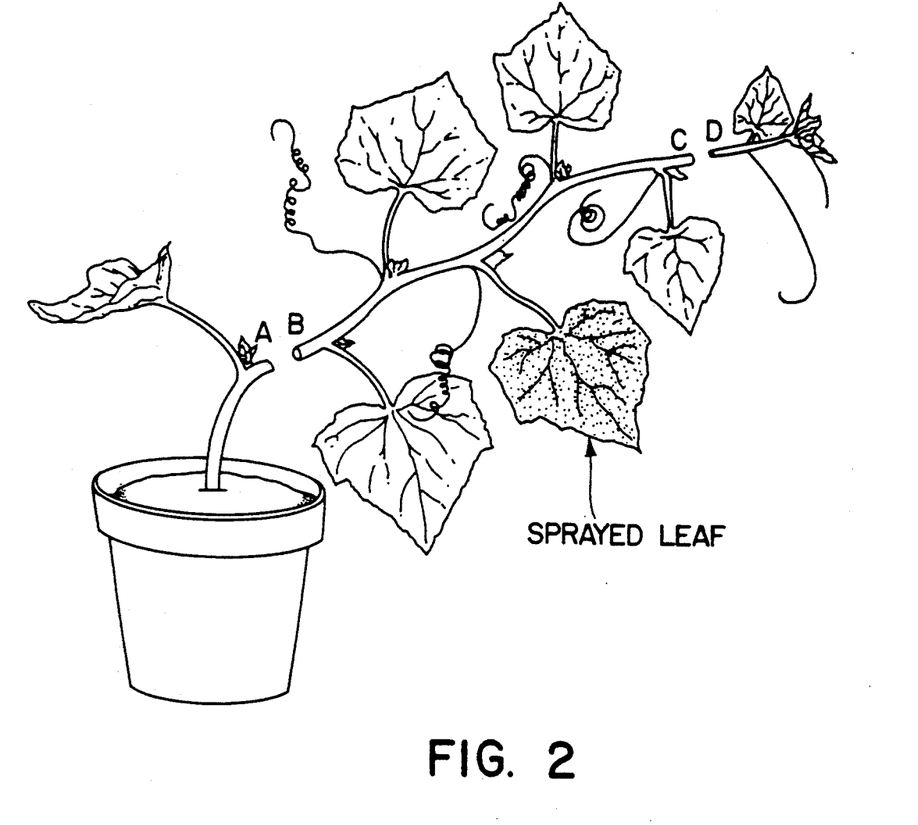
FIG. 2 shows a plant which has been cut as described in Table 2 for collecting exudate (10 $\mu l$ from each of 2 plants) from the cut stems of 31-day-old cucumber seedlings after single central leaf was sprayed with $H_2O$ or 100 $\mu g\ L^{-1}$ of L(+) adenosine and then plants excised at basal and apical ends within 5 seconds. The F value for interaction of position on the stem and control versus L(+) adenosine significant at $P \leq 0.01$ and $\leq 0.05$ for $Ca^{2+}$ and $K^+$, respectively. Each observation is the mean of six single plant replicates.

A single central leaf of cucumber plants which were about 100 cm long was sprayed with either water or 100 $\mu g\ L^{-1}$ of $L(+)$ adenosine. Subsequently, the stem was excised at basal and apical sites on the main axis as indicated in FIG. 2. Analysis of exudates from the four locations showed that the major effect was on the exudate from the base of the plant, however, higher $Ca^{2+}$ concentrations were measured from both basipetal and acopetal sides of the apical cut of the central stem (FIG. 2). The results are shown in Table 2.

TABLE 2

| Ion | Treatment | Position | | | |
|---|---|---|---|---|---|
| | | A | B | C | D |
| | | Conc (mM) | | | |
| $Ca^+$ | $H_2O$ | 2.59 | 1.13 | 0.70 | 0.65 |
| | $L(+)$ | 5.21** | 0.84 | 1.13* | 1.11* |
| $Mg^{2+}$ | $H_2O$ | 3.96 | 3.56 | 2.75 | 2.30 |
| | $L(+)$ | 5.50** | 3.15 | 3.28** | 2.92** |
| $K^+$ | $H_2O$ | 50.0 | 88.1 | 80.7 | 59.4 |
| | $L(+)$ | 64.5** | 80.9 | 79.5 | 72.8 |

*,**F value for comparison of $L(+)$ with $H_2O$ control significant at $P \leq .05$ and $.01$, respectively.

EXAMPLE 5

Figure 3:
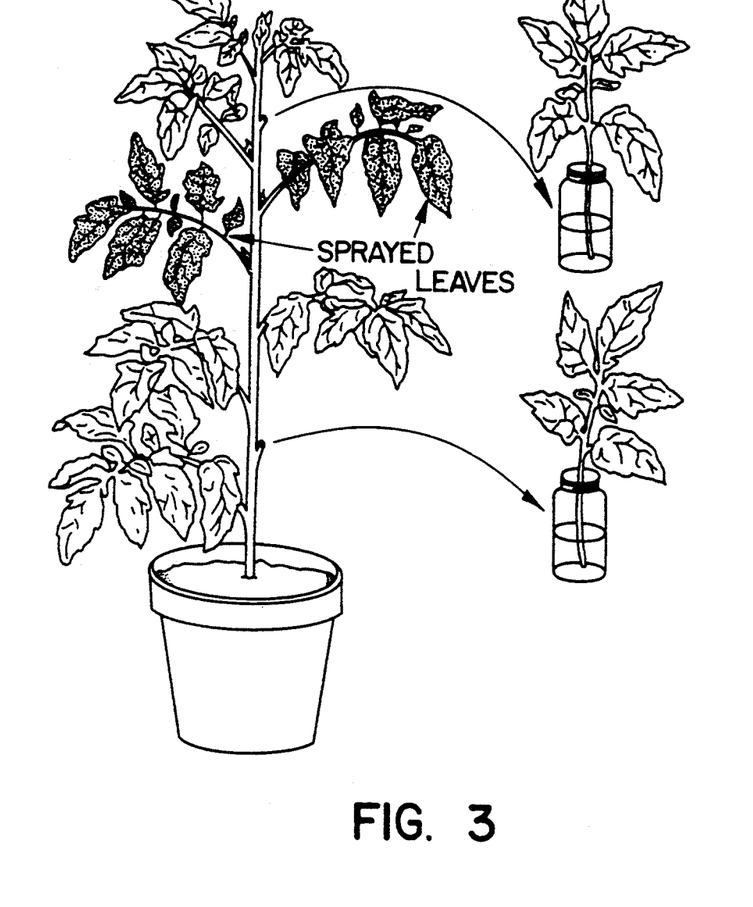
FIG. 3 shows a plant which has been cut as shown to determine the concentration of ions in the eluate from excised leaves of 50-day-old tomato plants whose central 2 leaves were sprayed with 100 $\mu g\ L^{-1}$ adenosine less than 5 seconds before the leaves were excised and placed in 5.0 ml of distilled water for 5 minutes. Each observation is mean of 10 single plant replicates.
Figure 4:
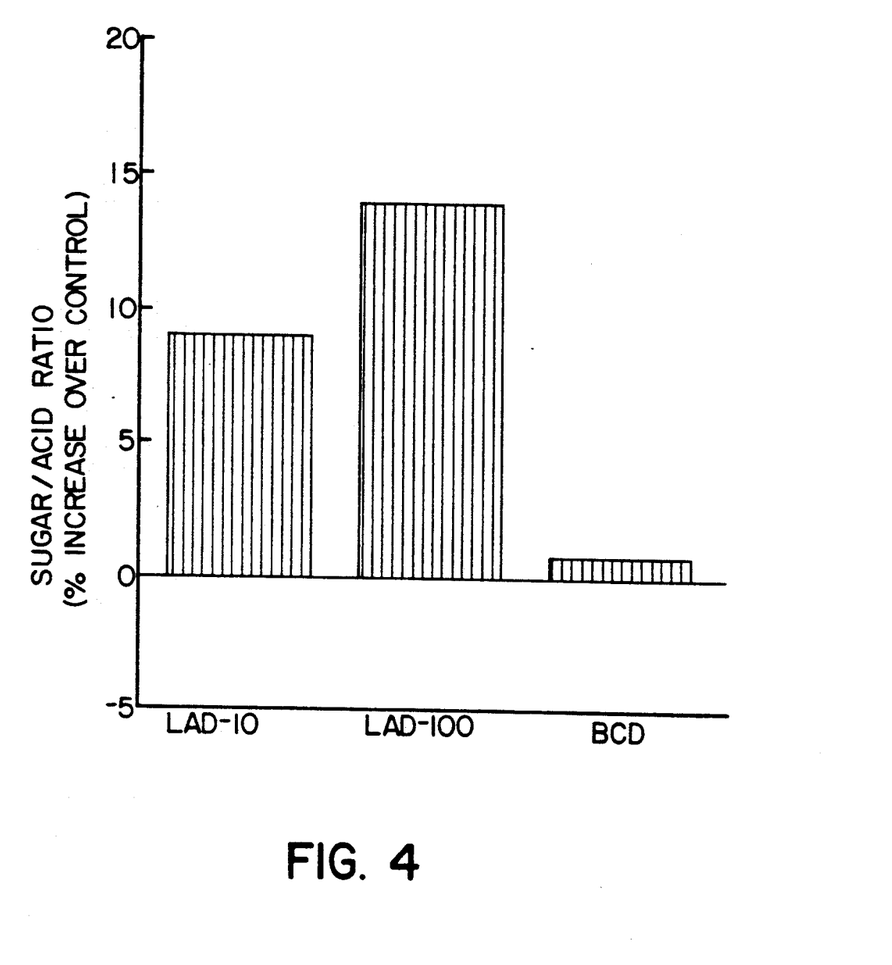
FIG. 4 is a bar graph showing the effect of L(+)adenosine (LAD) on the sugar to acid ratio in tomatoes when applied prior to harvest at concentrations of 10 and 100 $\mu g\ L^{-1}$ versus a control (water).

Two central leaves of tomato plants, as shown in FIG. 3, were sprayed with $L(+)$ adenosine and the apical and basal leaves were excised within 5 seconds and placed in distilled water for 5 minutes. The $L(+)$ adenosine increased the $Ca^{2+}$ and $Mg^{2+}$ concentration in the eluant from the petiole of apical leaves by 37 and 14%, respectively, whereas the $K^+$ concentration was 15% less in the $L(+)$ adenosine treatment (FIG. 4). The concentration of all ions from the eluant of the petioles from basal leaves was lower in $L(+)$ adenosine treatment. The results are shown in Table 3.

TABLE 3

| Treatment | Eluant (n moles g$^{-1}$ dry weight of leaflets) | | |
|---|---|---|---|
| | $Ca^{2+a}$ | $Mg^{2+a}$ | $K^{+b}$ |
| Apical | | | |
| $H_2O$ control | 35 | 68 | 611 |
| $L(+)$ adenosine | 49 | 106 | 480 |
| Basal | | | |
| $H_2O$ | 79 | 108 | 505 |
| $L(+)$ adenosine | 69 | 62 | 380 |

$^a$F value for interaction of position.
x treatment significant at $P \geq .01$.

EXAMPLE 6

When tomato plants were sprayed with $L(+)$ adenosine, and the shoots excised, the difference in concentration of $Ca^{2+}$ and $Mg^{2+}$ in the exudate of controls and $L(+)$ adenosine treatment in the sap exuding from the cut shoots was significantly different for at least 5.0 minutes (data not shown). In cucumber plants it was not possible to obtain more than about 10 $\mu l$ of sap from each cut because the exudate became too "gummy" to pick up with the pipette.

EXAMPLE 7

The stems of tomato plants were severed at different times after application of $L(+)$ adenosine to determine how long the treatment affected the flux of ions in the stem tissue. The concentration of $Ca^{2+}$ and $Mg^{2+}$ decreased linearly from 3 seconds to 200 minutes (FIG. 4). These tests indicated that the $L(+)$ adenosine induced a transitory redistribution of ions within stem tissue for 5 minutes after which the concentration of $Ca^{2+}$ and $Mg^{2+}$ the exudate came to equilibrium.

EXAMPLE 8

FIG. 4 shows the results of spraying green tomatoes with $L(+)$ adenosine (10 and 100 $\mu L^{-1}$) and then harvesting the tomatoes seven (7) days later. In FIG. 4, LAD is $L(+)$ adenosine. BCD is the carrier alone. FIG. 4 shows the increase in the sugar to acid ratio in the tomatoes. The green tomatoes were also stored at 80° F. (26.7° C.) in high humidity. The results are shown in Table 4.

TABLE 4

Storage Life of Tomatoes
Tomatoes sprayed and picked "Mature green" and stored at 80° F. in high humidity.

| $L(+)$ adenosine $\mu g$/liter | Days until 50% of Fruit rotted. Time (Days) |
|---|---|
| Control | 15 |
| 10.0 | 24 |
| 100 | 29 |

EXAMPLE 9

Redhaven peach trees, 4 years old with fruit and having a trained open center were treated with $L(+)$ adenosine thirty (30) days before the beginning of harvest (5 days harvest) before harvesting to determine the increase in firmness. A foliar spray of one-half gallon (1.89 liters) was applied to each tree. The results are shown in Table 5 wherein the "mean" represents the firmness in grams per square centimeter. Each mean is the average of four (4) trees.

TABLE 5

| Chemical | Concentration μg/liter | Firmness (gm/cm$^2$) |
|---|---|---|
| Control |  | 9.54 |
| Triacontanol | 2 | 9.13 |
| L(+) adenosine | 2 | 9.94 |
| Triacontanol | 18 | 10.25 |
| L(+) adenosine | 0.5 | 10.56 |
| Triacontanol | 10 | 10.82 |
| L(+) adenosine | 1.0 | 14.53 |

Thus 1 ppb of L(+) adenosine (trim) produced a 52% increase over the control. For all of the L(+) adenosine treatments of peaches the mean was 11.67 g/cm$^2$ or a 22% increase over the control.

EXAMPLE 10

The following Table 6 shows the effect of L(+) adenosine on Ca$^{+2}$ composition of "Flurry" pickling cucumbers in a Field test. The L(+) adenosine was applied twice at 168 hours and 48 hours before harvest at 100 μg per liter each application.

TABLE 6

Effect of L(+) adenosine on Ca$^{2+}$ composition of "Flurry" pickling cucumbers in a field test.
(g Ca$^{2+}$ g$^{-1}$ dry wt × 1000)

| Treatment | Pericarp Conc | Pericarp Total | Endocarp Conc | Endocarp Total | Total fruit |
|---|---|---|---|---|---|
| Water control | 19.6 | 849 | 8.29 | 116 | 966 |
| 100 μg/L L(+) adenosine | 19.7 | 863 | 9.09 | 129 | 992 |
| F value for comparison | NS | ≦.05 | ≦.05 | ≦.05 | NS |

The pericarp is between the epidermis and endocarp. The endocarp is around the seed cavity. The increase in Ca$^{2+}$ prevents "bloaters".

The calcium concentrations (2-4 mM) observed in the exudates in these studies are considered to be of apoplastic origin because the concentrations are several thousand times higher than the 200-400 nM concentrations reported for cytoplasm in plant cells, (Evans, D. E., et al., J. Exp. Bot. 42, 285 (1991)).

There is much evidence for Ca$^{2+}$ acting as a intracellular sensory system for numerous environmental stimuli such as insect and disease invasion, heat and cold shock, touching, wind and rain (Braam, J., et al., Cell 60, 357 (1990); and Mitchell, C. A., et al., J. Amer. Hort. Sci. 100, 161 (1975)). Gibberellic acid has been shown to be related to increases in intracellular free Ca$^{2+}$ in barley aleurone layers, and cytokinins increased intercellular Ca$^{2+}$ by activating plasma membrane ion channels (Schroeder, J. I., et al., The Plant Cell 3, 555 (1991)). It has also been suggested that calcium ions and calmodulin were involved in transduction of signals from the environment which enabled plants to sense and respond to environmental changes (Evans, D. E., et al., J. Exp. Bot. 42, 285 (1991)). However, there was no evidence in the preceding research for the changes in Mg$^{2+}$ and K$^+$ concentrations we have measured in tomato exudates.

A hypothesis that would explain the present invention is that nanomolar quantities of L(+) adenosine elicit membrane potentials or some other biophysical change, which results in specific release of ions in mmolar quantities from cell walls or other insoluble chelators within the stem and root apoplast. These ions may act in concert to initiate a cascade of enzyme or hormone activity, which results in the observed metabolic, dry weight changes and skin firmness.

It is intended that the foregoing description be only illustrative of the present invention and that the present invention be limited only by the hereinafter appended claims.

I claim:

1. A method for improving firmness or storage stability of a part which is to be removed from a plant selected from the group consisting of a fruit and a vegetable which comprises:
    (a) applying L(+) adenosine to the plant within 0.1 and 60 days before the part is removed in an amount sufficient to increase ion concentrations at extremities of the plant including the part; and
    (b) harvesting the part soon after the application to thereby improve the firmness or storage stability of the part.

2. The method of claim 1 wherein the L(+) adenosine is in water containing between about 0.01 and 10,000 μg/liter of L(+) adenosine.

3. The method of claim 1 wherein the plant part is a fruit.

4. The method of claim 3 wherein the plant part is a tomato as the fruit.

5. A method for inhibiting spoilage which is associated with a lack of firmness of a skin of the plant in a harvested part selected from the group consisting of a fruit and a vegetable severed from a plant which comprises:
    (a) applying L(+)adenosine to the plant within 0.1 to 60 days before the plant is harvested in an amount sufficient to increase puncture resistance of a skin of the part and to inhibit the spoilage of the part of the plant to be harvested; and
    (b) harvesting the plant part soon after the application.

6. The method of claim 5 wherein the L(+) adenosine is applied in water.

7. The method of claim 6 wherein the L(+) adenosine in water containing between about 0.01 and 10,000 μg/liter of L(+)adenosine.

8. The method of claim 5 wherein the part is a fruit.

9. The method of claim 8 wherein the part is a tomato.

* * * * *